(12) United States Patent
Lindgren et al.

(10) Patent No.: US 11,651,852 B2
(45) Date of Patent: May 16, 2023

(54) METHODS FOR SURGICAL GUIDELINE INDICATOR MAPPING TO FACILITATE AUTOMATED MEDICAL BILL ADJUDICATION AND DEVICES THEREOF

(71) Applicant: Mitchell International, Inc., San Diego, CA (US)

(72) Inventors: Valerie Q. Lindgren, San Diego, CA (US); Vicki L. Dunbar, San Diego, CA (US); Pamela Martinez, San Diego, CA (US)

(73) Assignee: Mitchell International, Inc., San Diego, CA (US)

( * ) Notice: Subject to any disclaimer, the term of this patent is extended or adjusted under 35 U.S.C. 154(b) by 4 days.

(21) Appl. No.: 16/989,781

(22) Filed: Aug. 10, 2020

(65) Prior Publication Data

US 2021/0043312 A1 Feb. 11, 2021

Related U.S. Application Data

(60) Provisional application No. 62/884,522, filed on Aug. 8, 2019.

(51) Int. Cl.
*G16H 40/20* (2018.01)
*G16H 50/70* (2018.01)
(Continued)

(52) U.S. Cl.
CPC ............ *G16H 40/20* (2018.01); *G06N 20/00* (2019.01); *G06Q 10/10* (2013.01); *G06Q 20/14* (2013.01);
(Continued)

(58) Field of Classification Search
CPC ......... G16H 40/20; G16H 20/40; G16H 70/20
See application file for complete search history.

(56) References Cited

U.S. PATENT DOCUMENTS

2015/0127370 A1* 5/2015 Cornelis ............... G06Q 10/10
705/2
2019/0139012 A1* 5/2019 Kube, II ............... G06Q 20/102

FOREIGN PATENT DOCUMENTS

WO WO-2012058242 A2 * 5/2012 ............. G16H 40/20

OTHER PUBLICATIONS

Bernard, S. P. (2008). Workflow key to real-time claims adjudication success. Healthcare Financial Management, 62(9), 88-91. Retrieved from https://dialog.proquest.com/professional/docview/196381410?accountid=131444 (Year: 2008).*

* cited by examiner

*Primary Examiner* — Linh Giang Le
*Assistant Examiner* — Constantine Siozopoulos
(74) *Attorney, Agent, or Firm* — Sheppard Mullin Richter & Hampton LLP

(57) ABSTRACT

Systems and methods are provided for automating the process of automatically determining appropriateness of surgical team services performed during a medical procedure. Clinical resource data with known surgical guideline indicator (SGIs) may be us used to generate and store a mapping of medical procedure codes to indications of the appropriateness of surgical team services corresponding to the medical procedure codes. A medical bill associated with an insurance claim may be analyzed to extract a medical procedure code corresponding to a surgical procedure, and an automated adjudication recommendation for the medical bill may be made based on the mapping between medical procedure codes and SGIs.

15 Claims, 9 Drawing Sheets

(51) Int. Cl.
*G06Q 20/14* (2012.01)
*G16H 70/20* (2018.01)
*G06Q 10/10* (2023.01)
*G06N 20/00* (2019.01)
*G06Q 50/26* (2012.01)
*G06Q 30/018* (2023.01)
*G06Q 40/08* (2012.01)

(52) U.S. Cl.
CPC ......... *G06Q 30/0185* (2013.01); *G06Q 40/08* (2013.01); *G06Q 50/26* (2013.01); *G16H 50/70* (2018.01); *G16H 70/20* (2018.01)

305

Centers for Medicare and Medicaid Services
Relative Value File

Provides indicators for reimbursement of Assistant At Surgery 310  0 = Payment restriction for assistants at surgery applies to this procedure unless supporting documentation is submitted to establish medical necessity 312  1 = Statutory payment restriction for assistants at surgery applies to this procedure. Assistants at surgery may not be paid.

314  2 = Payment restriction for assistants at surgery does not apply to this procedure. Assistants at surgery may be paid.

316  9 = Concept foes not apply

FIG. 3A

Centers for Medicare and Medicaid Services Relative Value File

307

Provides indicators for reimbursement of Co-Surgeon 320  0 =  Co-surgeons not permitted for this procedure 322  1 =  Co-surgeons could be paid. Supporting documentation is required to establish medical necessity of two surgeons for the procedure.

324  2 =  Co-surgeons permitted. No documentation is required if two specialty requirements are met.

326  9 =  Concept foes not apply

FIG. 3B

ASSISTANT AT SURGERY

| | CRITERIA |
|---|---|
| Assistant at Surgery meets industry guidelines for reporting | CPT procedure code meets definition of Surgical Procedure |
| | ACS Physicians as Assistants at Surgery Study = Almost Always |
| | CMS Relative Value File Assistant at Surgery = 2 |
| | Clinical staff reviewed and agrees |
| Assistant at Surgery does not meet industry guidelines for reporting | CPT procedure code meets definition of Surgical Procedure |
| | ACS Physicians as Assistants at Surgery Study = Almost Never |
| | CMS Relative Value File Assistant at Surgery = 0 |
| | Clinical staff reviewed and agrees |
| Assistant at Surgery does may or may not meet industry guidelines for reporting; Requires Review | CPT procedure code meets definition of Surgical Procedure |
| | ACS Physicians as Assistants at Surgery Study = Sometimes |
| | CMS Relative Value File Assistant at Surgery = 1 |
| | Clinical staff reviewed and agrees |
| Surgical Guideline Indicator concept does not apply (Out of Scope) | CPT procedure code does not meet definition of Surgical Procedure |
| | CPT procedure code cannot be confirmed as meeting definition of Surgical Procedure |
| | CMS Relative Value File Assistant at Surgery = 9 |
| | CMS Relative Value File Co-Surgeon = 9 |
| | Unlisted CPT procedure code |
| | Clinical staff reviewed and agrees |

FIG. 5A

| CO-SURGEON | |
|---|---|
| | CRITERIA |
| Assistant at Surgery meets industry guidelines for reporting | CPT procedure code meets definition of Surgical Procedure |
| | ACS Physicians as Assistants at Surgery Study = Almost Always |
| | CMS Relative Value File Assistant at Surgery = 1 |
| | Clinical staff reviewed and agrees |
| Assistant at Surgery may or may not meet industry guidelines for reporting; Requires Review | |
| Co-Surgeon meets industry guidelines for reporting | CPT procedure code meets definition of Surgical Procedure |
| | CMS Relative Value File Co-Surgeon = 2 |
| | Clinical staff reviewed and agrees |
| Co-Surgeon does not meet industry guidelines for reporting | CPT procedure code meets definition of Surgical Procedure |
| | CMS Relative Value File Co-Surgeon = 0 |
| | Clinical staff reviewed and agrees |
| Co-Surgeon may or may not meet industry guidelines for reporting; Requires Review | CPT procedure code meets definition of Surgical Procedure |
| | CMS Relative Value File Co-Surgeon = 1 |
| | Clinical staff reviewed and agrees |
| Surgical Guideline Indicator concept does not apply (Out of Scope) | CPT procedure code does not meet definition of Surgical Procedure |
| | CPT procedure code cannot be confirmed as meeting definition of Surgical Procedure |
| | CMS Relative Value File Assistant at Surgery = 9 |
| | CMS Relative Value File Co-Surgeon = 9 |
| | Unlisted CPT procedure code |
| | Clinical staff reviewed and agrees |

FIG. 5B

METHODS FOR SURGICAL GUIDELINE INDICATOR MAPPING TO FACILITATE AUTOMATED MEDICAL BILL ADJUDICATION AND DEVICES THEREOF

RELATED APPLICATIONS

This application claims the benefit of U.S. Provisional Application No. 62/884,522 filed on Aug. 8, 2019, the contents of which are incorporated herein by reference in its entirety.

TECHNICAL FIELD

The present disclosure is generally related to systems and methods for automating the determination of appropriateness of surgical team services, and more particularly, some embodiments relate to a systems and methods for implementing the same.

BACKGROUND

Insurance adjusters generally do not have the clinical background or expertise to determine whether an assistant at surgery or a co-surgeon is appropriate for particular surgical procedures associated with medical bills.

Existing technological tools used for process medical bills are incapable of effectively and efficiently rendering determinations whether utilization of surgical teams during surgical procedures identified on medical bills are appropriate and are limited to software searching tools. Furthermore, existing software tools only provide the user with the ability to manually search the appropriate guideline without a known automated solution in. As a result, the current process for determining whether surgical procedures performed by surgical teams are appropriate is time consuming and prone to errors, often resulting in missing and/or misidentified medical bills.

SUMMARY

In accordance with one or more embodiments, various features and functionality can be provided for automating the determination of appropriateness of surgical team services.

In some embodiments, a method may for surgical guideline indicator (SGI) mapping may facilitate automated medical bill adjudication. The method may by obtain clinical resource data with known SGIs to generate and store a mapping of medical procedure codes in the clinical resource data to indications of the appropriateness of surgical team services corresponding to the medical procedure codes. The obtained clinical resource data may include a plurality of clinical resource data sets respectively obtained from a plurality of clinical data sources. In some embodiments, the medical procedure codes may comprise current procedure terminology (CPT) codes.

In some embodiments, the method may determine more than one SGI for a CPT code based on the clinical resource data used. Upon determining that there is a disagreement between a SGI from the first set of clinical resource data and a second SGI from a second set of clinical resource data. The first and second SGIs may be associated with a same one of the medical procedure codes. For example, the first and second data sources may comprise a Centers for Medicare and Medicaid Services (CMS) relative value file and an American College of Surgeons (ACS) Physicians as Assistants at Surgery reference guide, respectively.

In some embodiments, the method may analyze an electronic medical bill associated with an insurance claim to extract a medical procedure code corresponding to a surgical procedure associated with the electronic medical bill.

In some embodiments, the method may generate an automated adjudication recommendation for the medical bill based on a comparison of the extracted medical procedure code to the stored mapping.

In some embodiments, the method may obtain clinical review data comprising the indication of the appropriateness of surgical team services for one of the surgical procedures corresponding to the one of the medical procedure codes, when the determination indicates there is a disagreement between the first SGI and the second SGI.

In some embodiments, the indications of the appropriateness of using surgical team services (e.g., an assistant at surgery or a co-surgeon) during a surgical procedure may comprise one or more of an indication that industry guidelines for reporting are met, industry guidelines for reporting are not met, or industry guidelines for reporting may be met.

Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any inventions described herein, which are defined solely by the claims attached hereto.

BRIEF DESCRIPTION OF THE DRAWINGS

FIG. 3A illustrates example SGIs used for assistants at surgery services, according to an implementation of the disclosure.

FIG. 3B illustrates example SGIs used for co-surgeon services, according to an implementation of the disclosure.

FIG. 5A illustrates example criteria for determining appropriateness of assistant at surgery services, according to an implementation of the disclosure.

FIG. 5B illustrates example criteria for determining appropriateness of co-surgeon services, according to an implementation of the disclosure.

DETAILED DESCRIPTION

Figure 1:
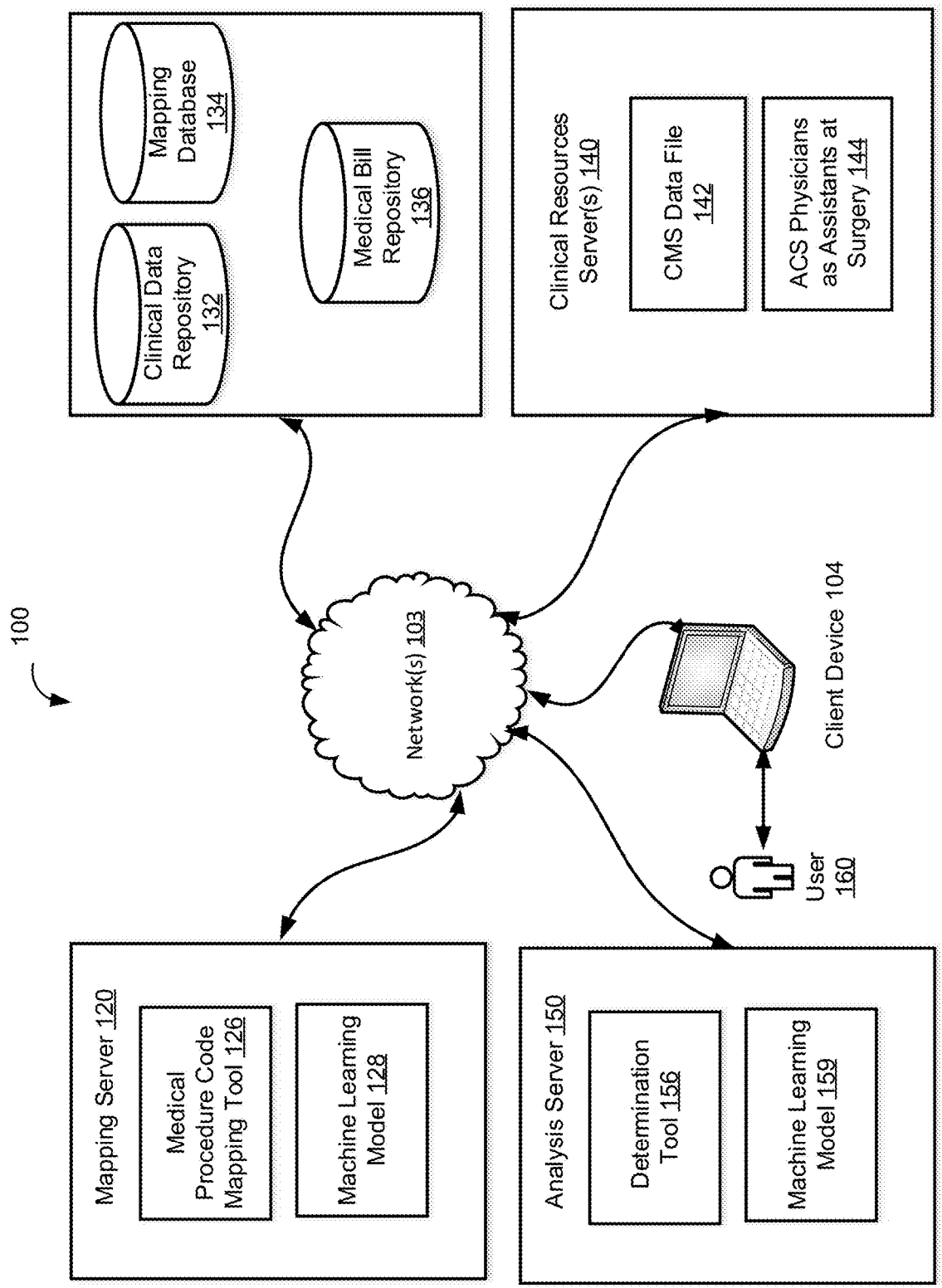
FIG. 1 illustrates an example automated surgical team services appropriateness determination system, according to an implementation of the disclosure.

Described herein are systems and methods for automating the process of automatically determining appropriateness of surgical team services performed during a medical procedure. The details of some example embodiments of the systems and methods of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

As alluded to above, insurance adjuster are not always able to determine whether services performed by a surgical team (e.g., assistants at surgery, co-surgeon, assistant surgeon and so on) should be reimbursed. In particular, under some circumstances, highly complex procedures may require the services of a surgical team, consisting of several physicians, often of different specialties, plus other highly skilled, specially trained personnel and complex equipment. A physician operating in this setting is referred to as a team surgeon. Co-Surgeons are defined as two or more surgeons, where the skills of both surgeons are necessary to perform distinct parts of a specific operative procedure. Co-surgery is always performed during the same operative session. An assistant surgeon is defined as a physician who actively assists the operating surgeon. An assistant may be necessary because of the complex nature of the procedure(s) or the patient's condition. The assistant surgeon is usually trained in the same specialty. An assistant-at-surgery may be a physician assistant, nurse practitioner or nurse midwife acting under the direct supervision of a physician, where the physician acts as the surgeon and the assistant-at surgery as an assistant.

Various insurance payers when determining whether the use of surgical team services is appropriate relies on stored surgical guideline indicators (SGI). SGIs may be used to indicate whether surgical team services used during a particular surgical procedure (i.e., a surgical procedure having a particular code) meet industry guidelines for reimbursement. SGIs are associated with individual medical procedure codes CPT codes, generally in the 10000-69999 range or current procedure terminology (CPT) codes.

Embodiments of the disclosed technology provide a tool for automating the mapping of SGIs to medical procedure codes. The tool utilizes existing associations. The tool may also provide mechanisms to review the association results, which can then be accepted or rejected based on a particular protocol or threshold. For example, the tool may programmatically map procedure codes by using known associations between SGI medical procedures. In some embodiments, machine learning models may be employed to determine associations between SGIs and medical procedure codes, as described in detail below. Furthermore, a tool for automating a determination whether use of surgical team is appropriate utilizes the associations between SGIs and medical procedure codes.

The automatic mapping of SGIs to medical procedure codes provides several advantages. For example, using the mapping of SGI to medical procedure codes allows to automate the appropriateness of surgical team services performed during a medical procedures determination. results in a reduction in human effort, which in turn reduces cost and increases throughput and adjudication accuracy.

System

FIG. 1 illustrates an automated surgical team services appropriateness determination system 100 according to some embodiments of the disclosed technology. In some embodiments, system 100 may include a mapping server 120, an analysis server 150, a clinical document repository 132 configured to store clinical resource data including medical procedures with assigned surgical guideline indicator (SGI), a mapping database 134 configured to store associations between medical procedure codes and surgical guideline indicators (SGI), as described above, a medical bill database 134 configured to store medical bills submitted for insurance adjustment and other related information, a one or more clinical resources services server(s) 140 (e.g., CMS server(s) 142, ACS Physicians as Assistants at Surgery server(s) 144), and other such similar servers), a network 103, and a client computing device 104. A user 160 may be associated with client computing device 104 as described in detail below. Additionally, system 100 may include other network devices such as one or more routers and/or switches.

In some embodiments, client computing device 104 may include a variety of electronic computing devices, for example, a smartphone, a tablet, a laptop, a display, a mobile phone, a computer wearable device, such as smart glasses, or any other head mounted display device, or a combination of any two or more of these data processing devices, and/or other devices.

In some embodiments, mapping server 120 and analysis server 150 may each include a processor, a memory, and network communication capabilities. In some embodiments, mapping server 120 and analysis server 150 may each be a hardware server. In some implementations, mapping server 120 and analysis server 150 may each be provided in a virtualized environment, e.g., mapping server 120 and/or analysis server 150 may be a virtual machine that is executed on a hardware server that may include one or more other virtual machines. Additionally, in one or more embodiments of this technology, virtual machine(s) running on mapping server 120 and/or analysis server 150 may be managed or supervised by a hypervisor. Mapping server 120 and analysis server 150 may be communicatively coupled to network 103.

In some embodiments, the memory of mapping server 120 may store application(s) that can include executable instructions that, when executed by mapping server 120, cause mapping server 120 to perform actions or other operations as described and illustrated below with reference to FIGS. 2A-2B. For example, mapping server 120 may include a medical procedure code mapping tool 126. The memory of analysis server 150 may store application(s) that can include executable instructions that, when executed by analysis server 150, cause analysis server 150 to perform actions or other operations as described and illustrated below with reference to FIG. 4. For example, analysis server 150 may include a determination tool 156.

In some embodiments, medical procedure code mapping tool 126 and determination tool 156, may be each implemented as one or more software packages executing on one or more mapping server 120 and analysis server 150 computers, respectively. For example, a client application implemented on one or more client computing device 104 as client mapping tool application and determination application.

In some embodiments, medical procedure code mapping tool 126 and determination tool 156 may each be a server application, a server module of a client-server application, or a distributed application. In some embodiments, medical procedure code mapping tool 126 and determination tool 156 may each be implemented using a combination of hardware and software. The application(s) can be implemented as modules, engines, or components of other application(s). Further, the application(s) can be implemented as operating system extensions, module, plugins, or the like.

Even further, the application(s) may be operative locally on the device or in a cloud-based computing environment. The application(s) can be executed within or as virtual machine(s) or virtual server(s) that may be managed in a cloud-based computing environment. Also, the application(s), and even the mapping or analysis computing devices themselves, may be located in virtual server(s) running in a cloud-based computing environment rather than being tied to one or more specific physical network computing devices. Also, the application(s) may be running in one or more virtual machines (VMs) executing on the mapping and analysis computing devices.

In some embodiments, clinical data repository 132 may include one or more databases, which may store data related to medical procedure codes corresponding to surgical procedures associated with medical bills.

In some embodiments, mapping database 134 may include one or more database, which may store association data related to manually completed mapping, automatically completed mapping, data related to incomplete or in progress mapping, and the like. In some embodiments, system 100 may employ one or more machine learning models 128, which may execute on mapping server 120.

In some embodiments, mapping server 120 and analysis server 150 may transmit and receive information to and from client computing device 104, one or more clinical resources servers 140, and/or other servers via network 103. For example, a communication interface of the mapping server 120 and analysis server 150 may be configured to operatively couple and communicate between clinical data repository 132, mapping database 134, medical bill database 136, client computing device 104, clinical resources servers 140, which are all coupled together by the communication network(s) 103.

In some embodiments, medical procedure code mapping tool 126 and determination tool 156 may each access clinical data repository 132, mapping database 134, and medical bill database 136 over a network 130 such as the Internet, via direct links, and the like.

In some embodiments, mapping server 120 and analysis server 150 may each be a standalone device or integrated with one or more other devices or apparatuses, such as one or more of the storage devices, for example. For example, mapping server 120 and analysis server 150 may each include or be hosted by one of the storage devices, and other arrangements are also possible.

In some embodiments, clinical resources servers 140 may be configured to store resource data that includes at least a correlation between medical procedure codes and SGIs, which include indicators for reimbursement for the use of surgical team services during surgical procedures associated with the medical procedure codes. In some embodiments, clinical resources servers 140 may include Medicare and Medicaid Services (CMS) data file(s) 142 configured to store, among other data, relative value files that includes the correlation between medical procedure codes and SGI. Additionally, clinical resources servers 140 may include American College of Surgeons (ACS) Physicians as Assistants at Surgery publication 144 configured to store, manage, and process information related to correlations between surgical procedure codes and SGIs. In some embodiments, clinical resources servers 140 may be configured to communicate with additional disparate third-party services (e.g., medical, regulatory, and such similar providers) to request and receive data regarding medical procedures, criteria for using surgical team during particular procedure, and indicator assigned to particular procedure codes.

In some embodiments, each of clinical resources servers 140, CMS data file(s) 142, and ACS Physicians as Assistants at Surgery publication 144 may include any type of computing device that can be used to interface with mapping server 120 and/or medical procedure code mapping tool 126, document repository 132, mapping databases 134, medical bill database 136, other clinical resources servers 140, and client computing device tool 104. For example, each of clinical resources servers 140, CMS data file(s) 142, and ACS Physicians as Assistants at Surgery data file(s) 144 may include a processor, a memory, and a communication interface, which are coupled together by a bus or other communication link, although other numbers and/or types of network devices could be used. In some embodiments, each of clinical resources servers 140, CMS data file(s) 142, and ACS Physicians as Assistants at Surgery publication 144 may also include a database.

In some embodiments, mapping server 120, analysis server 150, clinical resources servers 140, CMS data file(s) 142, and ACS Physicians as Assistants at Surgery publication 144, and or other components may be a single device. Alternatively, a plurality of devices may be used. For example, the plurality of devices associated with clinical resources servers 140, CMS data file(s) 142, and ACS Physicians as Assistants at Surgery publication 144 may be distributed across one or more distinct network computing devices that together comprise one or more clinical resources servers 140, CMS data file(s) 142, and ACS Physicians as Assistants at Surgery publication 144.

In some embodiments, mapping server 120, analysis server 150, clinical resources servers 140, CMS data file(s) 142, and ACS Physicians as Assistants at Surgery publication 144 may not be limited to a particular configuration. Thus, in some embodiments, mapping server 120, analysis server 150, clinical resources servers 140, CMS data file(s) 142, and ACS Physicians as Assistants at Surgery publication 144 may contain a plurality of network devices that operate using a master/slave approach, whereby one of the network devices operate to manage and/or otherwise coordinate operations of the other network devices. Additionally, in some embodiments, mapping server 120, analysis server 150, clinical resources servers 140, CMS data file(s) 142, and ACS Physicians as Assistants at Surgery publication 144 may comprise different types of data at different locations.

In some embodiments, mapping server 120, clinical resources servers 140, analysis server 150, CMS data file(s) 142, and ACS Physicians as Assistants at Surgery publication 144 may operate as a plurality of network devices within a cluster architecture, a peer-to-peer architecture, virtual machines, or within a cloud architecture, for example. Thus, the technology disclosed herein is not to be construed as being limited to a single environment and other configurations and architectures are also envisaged.

Although the exemplary network environment 100 with client computing device 104, mapping server 120, analysis server 150, clinical resources servers 140, CMS data file(s) 142 and ACS Physicians as Assistants at Surgery publication 144, and network(s) 103 are described and illustrated herein, other types and/or numbers of systems, devices, components, and/or elements in other topologies can be used. It is to be understood that the systems of the examples described herein are for exemplary purposes, as many variations of the specific hardware and software used to implement the examples are possible, as will be appreciated by those skilled in the relevant art(s).

One or more of the devices depicted in the network environment, such as client computing device 104, mapping server 120, analysis server 150, clinical resources servers 140, CMS data file(s) 142 and ACS Physicians as Assistants at Surgery publication 144 may be configured to operate as virtual instances on the same physical machine. In other words, one or more of client computing device 104, mapping server 120, analysis server 150, clinical resources servers 140, CMS data file(s) 142, and/or ACS Physicians as Assistants at Surgery publication 144 may operate on the same physical device rather than as separate devices communicating through communication network(s). Additionally, there may be more or fewer devices than client computing device 104, mapping server 120, analysis server 150 clinical resources servers 140, CMS data file(s) 142 and ACS Physicians as Assistants at Surgery publication 144.

In addition, two or more computing systems or devices can be substituted for any one of the systems or devices, in any example set forth herein. Accordingly, principles and advantages of distributed processing, such as redundancy and replication also can be implemented, as desired, to increase the robustness and performance of the devices and systems of the examples. The examples may also be implemented on computer system(s) that extend across any suitable network using any suitable interface mechanisms and traffic technologies, including, by way of example, wireless networks, cellular networks, PDNs, the Internet, intranets, and combinations thereof.

As alluded to earlier, adjudication of medical bills requires clinical knowledge associated with determining appropriateness of use of surgical team during a surgical procedure. Conventionally, a user performing the determination may be forced to manually assign a surgical guideline indicators (SGIs) to a procedure in review indicating whether any payment restrictions must be applied during reimbursement. To accomplish this, the user may be forced to reference disparate sources provide information about what SGI applies to what procedure based on a medical procedure code (e.g., current procedure terminology (CPT) codes) associated with the procedure. This process is known to be labor intensive and costly.

By virtue of automatically generating a mapping base that stores associations between medical procedure codes associated with surgical procedures and SGIs, results in subsequent automation of the medical bill adjudication process. That is, the by referencing the mapping base eliminates the need for skilled user having to determine appropriateness of surgical team services during a surgical procedure, which in turn results in significant cost savings and improves data reliability and accuracy. Additionally, by using multiple correlated source of clinical resource data during the mapping process increases accuracy of the appropriateness determination. For example, FIG. 2 illustrates a process 200 for automatically associating medical procedure codes with SGIs according to some embodiments of the disclosed technology.

The process 200 may begin with obtaining clinical resource data from a clinical data database 250 at 201. As explained above, clinical data repository 250 may be populated with data from one or more clinical resource servers 140, as illustrated in FIG. 1. In some embodiments, clinical resource data may include disparate sets of data obtained from multiple data sources (e.g., a CMS relative value file provided by CMS data file 142 and an ACS Physicians as Assistants at Surgery reference guide provided by ACS Physicians as Assistants at Surgery publication 144, illustrated in FIG. 1). Other types of sources of clinical resource data can also be used in other examples. By virtue of using multiple sources of clinical resource data during the mapping process results in a more accurate associations between medical procedure codes and SGIs.

The clinical resource data may include SGIs expressed as integer or other values. The value of the SGI may indicate whether surgical team services used during a particular surgical procedure (i.e., a surgical procedure having a particular code) meet industry guidelines for reimbursement.

For example, FIG. 3A illustrates an exemplary table 305 of SGIs 310, 312, 314, and 316 used for assistants during surgery based on Centers for Medicare and Medicaid Services (CMS) relative value data. SGIs 310, 312, 314, and 316 may include respective integer values 0, 1, 2, and 9 values. SGIs 310, 312, 314, and 316 may be used for procedure codes (e.g., CPT codes, generally in the 10000-69999 range or CPT Category III section of the American Medical Association's CPT code book). SGI 310 and 312 with respective values 0 and 1 indicate that there is a payment restriction for assistants during a particular surgical procedure, while SGI 314 with a value of 2 indicates that no payment restriction apply during a particular surgical procedure. Finally, SGI 316 with a value of 9 indicates that reimbursement is inapplicable for assistants during a particular surgical procedure.

Similarly, FIG. 3B illustrates an exemplary table 307 of SGIs 320, 322, 324, and 326 for co-surgeons during surgery based on the CMS relative value data. Similar to the example illustrated in FIG. 3A, SGIs 320, 322, 324, and 326 may include respective integer values 0, 1, 2, and 9 values. SGI 320 and 322 with respective values 0 and 1 indicate that there is a payment restriction for co-surgeons during a particular surgical procedure, while SGI 324 with a value of 2 indicates that no payment restriction apply during a particular surgical procedure. Finally, SGI 326 with a value of 9 indicates that reimbursement is inapplicable for co-surgeons during a particular surgical procedure. In some embodiments, other types of SGIs having other meanings and correlated with other types of information and codes can also be included in the clinical resource data in other examples.

Referring back to FIG. 2A, in step 201, SGIs associated with the same medical procedure codes are extracted from different sets of clinical resources. For example, information from several reliable sources (e.g., CMS Relative Value File and ACS Physicians as Assistants at Surgery Study) may be combined and stored in a database. In some embodiments, the data may be correlated based on the SGIs for specified CPT procedure codes to provide automated functionality that can be used to adjudicate surgical bills. For example, CPT procedure codes may be reviewed and assigned as either "meeting industry reporting guidelines", "not meeting industry reporting guidelines", or "may/may not meet industry reporting guidelines" based on one or more sets of criteria. In some embodiments, the SGI correlations may be performed by way of using definitions and criteria for correlation and mapping. For those procedures where the industry guidelines disagree, the procedure may be reviewed for appropriateness of mapping by clinical staff.

In step 203, the SGI associated with the same medical procedure codes are compared to determine whether there is a disagreement between the correlated SGIs from different sets of clinical resource data for the same medical procedure code.

For example, a disagreement can include when one SGI corresponds with a payment restriction for an assistant at surgery and another SGI associated with the same medical procedure code may indicate that payment is not restricted. In another example, one SGI may indicate that payment is not restricted for a co-surgeon and another SGI associated with the same medical procedure code may indicate that payment may be restricted. Other types of disagreements can also be determined in step 203. Upon determining that there is no disagreement between a first SGI from a first set of clinical resource data and a second SGI associated with the same medical procedure code and from a second set of clinical resource data, then the Yes branch is taken to step 206.

In step 206, the clinical resource data involved in the disagreement, or at least a portion thereof, may be presented to a skilled user (e.g., clinical staff). Upon review by the user, the determination as to which SGI is accurate may be received at step 205. Accordingly, the user may perform a manual clinical review in order to determine the appropriateness, and associated payment restriction, if any, for an assistant at surgery and/or a co-surgeon for the medical procedure code when there is a variation between SGIs associated with medical procedure codes obtained from disparate sources. Subsequent to receiving the clinical review data, or upon determining that there is no disagreement between SGIs and medical procedure code associations in step 203, the "No" branch is taken to step 205.

In some embodiments, the system may perform the "absolute" portion of review. For example, adjusters (users) will only need to review those CPT procedure codes that may or may not meet industry guidelines for Assistant at Surgery and/or Co-Surgeon. The criteria for performing the review may be based on level of reimbursement, among other factors.

In step 205, the association between the SGI (indicating the appropriateness of using assistant at surgery and/or a co-surgeon services) and the medical procedure code is stored in SGI mapping database 255. The indications the appropriateness of an assistant at surgery or a co-surgeon for the surgical procedure associated with the medical procedure code include an indication that industry guidelines for reporting are met, industry guidelines for reporting are not met, or industry guidelines for reporting may be met.

Figure 2A:
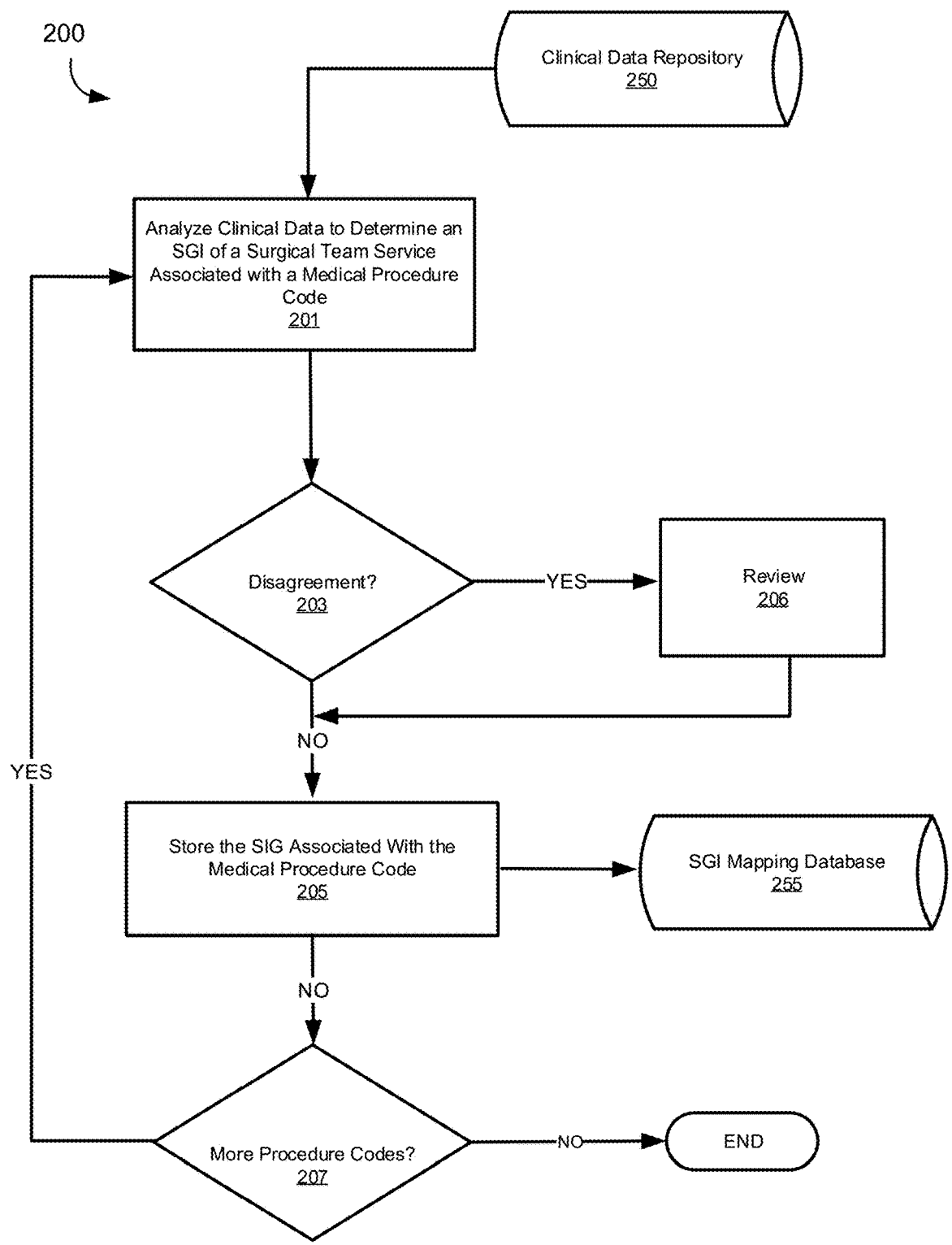
FIG. 2A illustrates an example process for automating the assignment of surgical guideline indicators (SGI) to medical procedure codes, according to an implementation of the disclosure.
Figure 2B:
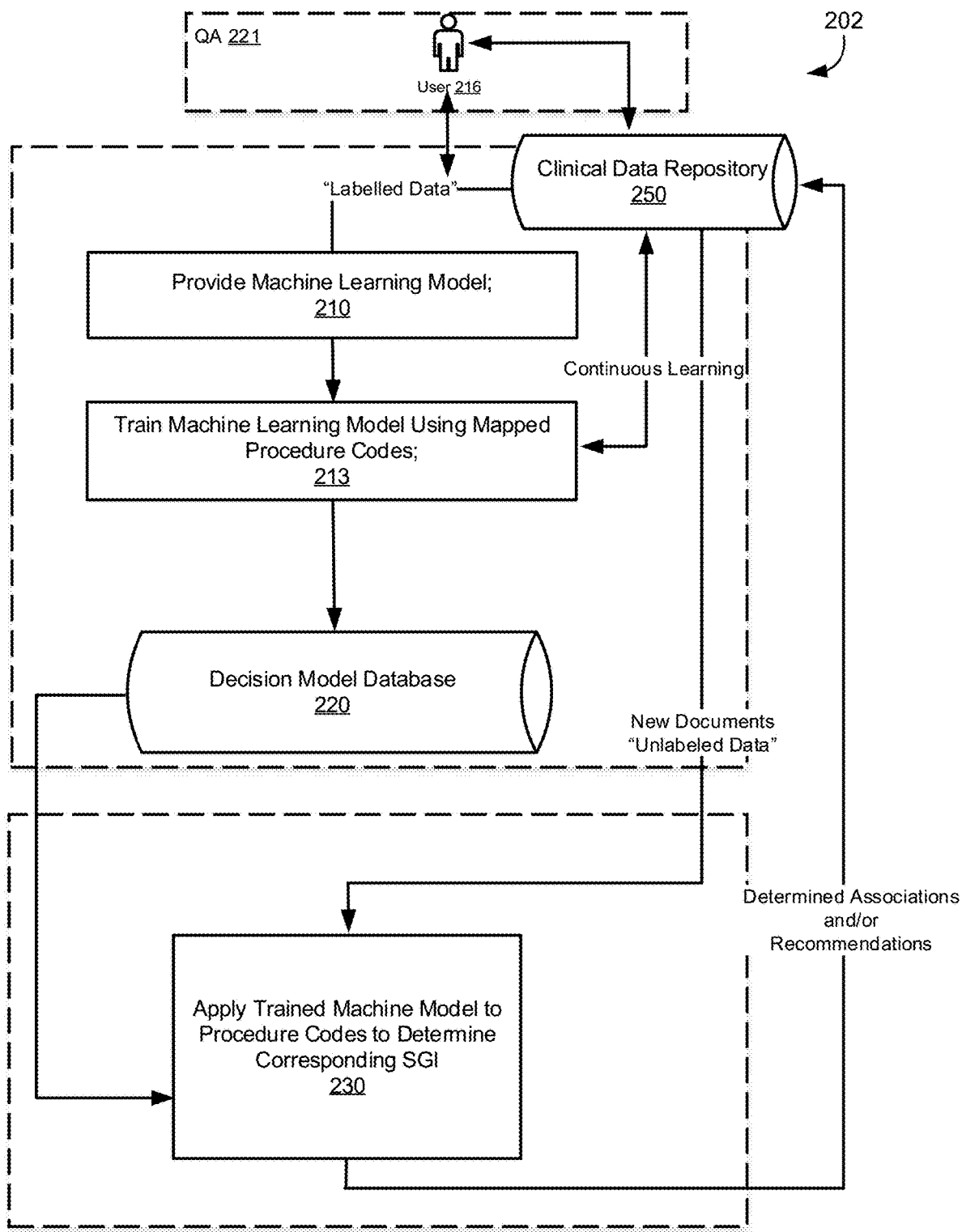
FIG. 2B illustrates an example process for using a machine learning module to assign surgical guideline indicators (SGI) to medical procedure codes, according to an implementation of the disclosure.

FIG. 2B illustrates example process of determining an appropriate SGI for a medical procedure codes according to an implementation of the disclosure using a machine learning model. Other artificial intelligence techniques may be used instead of, or in addition to, using a machine learning model. By virtue of utilizing a machine learning approach enhances the automated mapping process described herein. In particular, by using machine learning model, allows the system to associate a medical procedure code that may not have been assigned a SGI.

The process 202 may include applying a machine learning model, at 210. The machine learning model may be any machine learning mode, algorithm, or an Artificial Intelligence (AI) technique, capable of the functions described herein. The process 202 may include training the machine learning model, at 213. For example, specific keywords, phrases, diagnoses, medical procedures and/or other data elements, for the previously associated medical procedure codes may be applied as inputs to the machine learning model. Training the machine learning model may include supervised learning, unsupervised learning, or combinations thereof. During the training stage, process 202 may include the machine learning model storing the values related to the decisions made during the training stage in a decision model database 220.

After training, the machine learning model may be used to associate "unlabeled" data, i.e., any medic procedure code in a medical bill. The machine learning model may utilize the decision data values that are determined to be related to data in medical bill from a decision model database 220 when determining the new associations between an unmapped repair document for any vehicle and any vehicle part and/or labor operation, at 230. For example, the machine learning model may identify keyword and phrases in the repair document and determine if matches exist between the values stored in decision model database 220 when making the determination. Depending on match reliability, the machine learning model may create accurate associations for unlabeled repair documents.

In cases where associations determined by process 202 are inaccurate, user 216 may manually reject the associated mapping and that rejected associated mapping may in turn be fed back to the model for further relearning and as re-tuning the machine learning model for enhanced accuracy of future predictions. The relearned model may then be redeployed and utilized again to update and complete the mapping process with enhanced precision.

As alluded to above, the mapping database, populated by automatically associating medical procedure codes with SGIs, illustrated in FIG. 2A, may be utilized during the determination of appropriateness of using surgical team services (e.g., assistant at surgery services or co-surgeon services) according to some embodiments of the disclosed technology.

Figure 4:
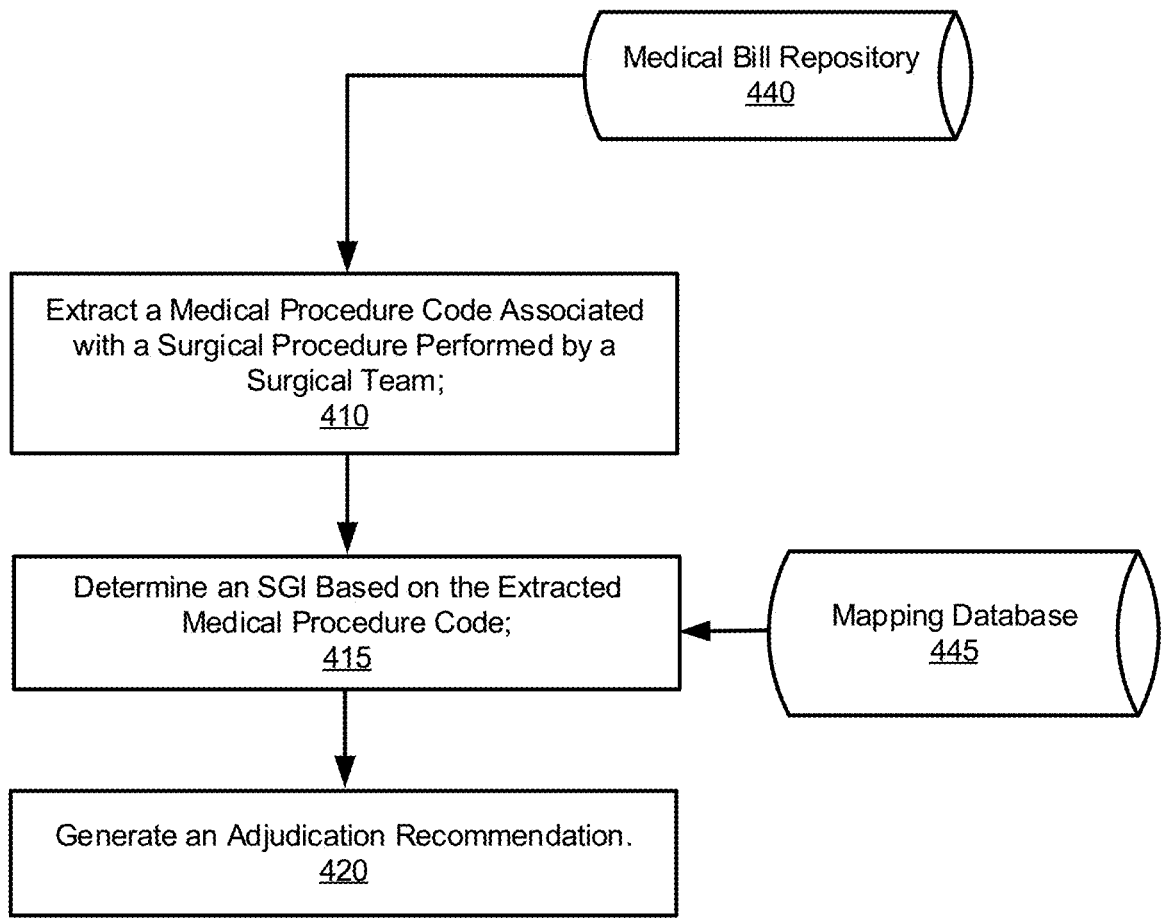
FIG. 4 illustrates an example process for automating the determination of appropriateness of surgical team services, according to an implementation of the disclosure.

For example, FIG. 4 illustrates a process 400 for automatically determining appropriateness of reimbursement for surgical team services during a surgical procedure associated with a particular medical procedure code. The process may begin by receiving an adjudication request for an electronic medical bill. In some embodiments, the electronic medical bill may be stored awaiting automatic analysis within medical bill repository 440.

In step 410, a medical procedure code (e.g., CPT code), corresponding to a surgical procedure, may be extracted from the received electronic medical bill associated with an insurance claim. For example, stored optical character recognition programmed instructions may be utilized to extract the CPT code from the medical bill.

In step 415, the SGI mapping database 445 (e.g., mapping database illustrated in FIG. 2A), may be used to determine an SGI based on the extracted medical procedure code. In some embodiments, payment information related to payments made to surgical team members (e.g., assistant at surgery and/or a co-surgeon) may be extracted and used to determine the corresponding SGI. Upon determining a medical procedure code in the SGI mapping database 445 by using the extracted medical procedure code, the corresponding SGI, indicating the appropriateness of using surgical team services during a surgical procedure, may be obtained and stored in stored in a data field related to the medical bill in the medical bill repository 440.

By virtue of using the mapping database 445, allows the medial bills to be adjudicated bills more efficiently. That is, the corresponding SGI determined for a particular medical procedure code is based on the previously correlated data using criteria and stored in the mapping database 445, as described with reference to FIG. 2A.

This eliminates the need for manual confirmation. For example, whether a particular CPT procedure code is a surgical CPT procedure code, or if a modifier (62, 80, 81, 82, AS) is appropriate for appending to a CPT procedure code. Furthermore, by automatically determining the SGI for each medical procedure eliminates the need to individually review industry guideline resources to confirm appropriateness of using services of a surgical team member (i.e., Assistant at Surgery and/or Co-Surgeon).

In some embodiments, if the SGI cannot be determined, a flag identifying the medical bill as undeterminable or inconclusive may be generated and stored in a data field related to the medical bill in the medical bill repository 440. Additionally, a notification may be generated alerting skilled users that further review may be required. That is, an adjuster will only need to review those CPT procedure codes that may or may not meet industry guidelines for Assistant at Surgery and/or Co-Surgeon.

In step 420, adjudication recommendation for the medical procedure utilizing surgical team services based on the indication obtained in step 415 may be determined. The adjudication recommendation may be output to a source of the adjudication request, such as one of the adjuster devices, for example, and can include an indication of whether reimbursement for an assistant at surgery and/or a co-surgeon for the surgical procedure associated with the medical bill is appropriate, although other information can also be output in step 420 in other examples.

Referring to FIG. 5A, exemplary criteria used to determine the appropriateness of an assistant at surgery for surgical procedures corresponding to medical procedure codes, and the associated indication, is illustrated. In one example illustrated in FIG. 5A, the indication corresponds with meeting industry guidelines for reporting when a CPT code meets the definition of a surgical procedure, the ACS Physicians as Assistants at Surgery Study includes an "almost always" SGI and the CMS relative value file. Definitions and criteria for database development are absolute requirements for support of the SGI recommendations and for future mapping and maintenance of the data. For all newly added procedure codes (this is done typically on an annual or quarterly basis), review for inclusion in the database is required and will be based on the developed definitions and criteria. These definitions and criteria also form the basis for support of the surgical guideline recommendations when queried by the end user.

Referring to FIG. 5B, exemplary criteria used to determine the appropriateness of a co-surgeon for surgical procedures corresponding to medical procedure codes is illustrated. In one example illustrated in FIG. 5B, the indication corresponds with not meeting industry guidelines for reporting when a CPT code meets the definition of a surgical procedure and the CMS relative value file includes a "0" SGI correlated with the medical procedure code for the surgical procedure. Other types of criteria for establishing the indications of the appropriateness of an assistant at surgery and/or a co-surgeon correlated to a medical procedure code in the stored mapping can also be used in other examples.

In some embodiments, steps 410-420 can be repeated for any number of electronic medical bills identified in the received adjudication request. During a batch processing of electronic medical bills, a flag or other indication may be attached to the output adjudication decision for those of the medical bills not adjudicated conclusively, such as those for which the adjudication decision is that industry guidelines for reporting may be met. In some embodiments, an assistant at surgery or a co-surgeon may or may not be permitted during a surgical procedure based on the content of supporting documents, for example, for such medical bills, which therefore require an additional review, such as by a user of one of the adjuster devices.

Figure 6:
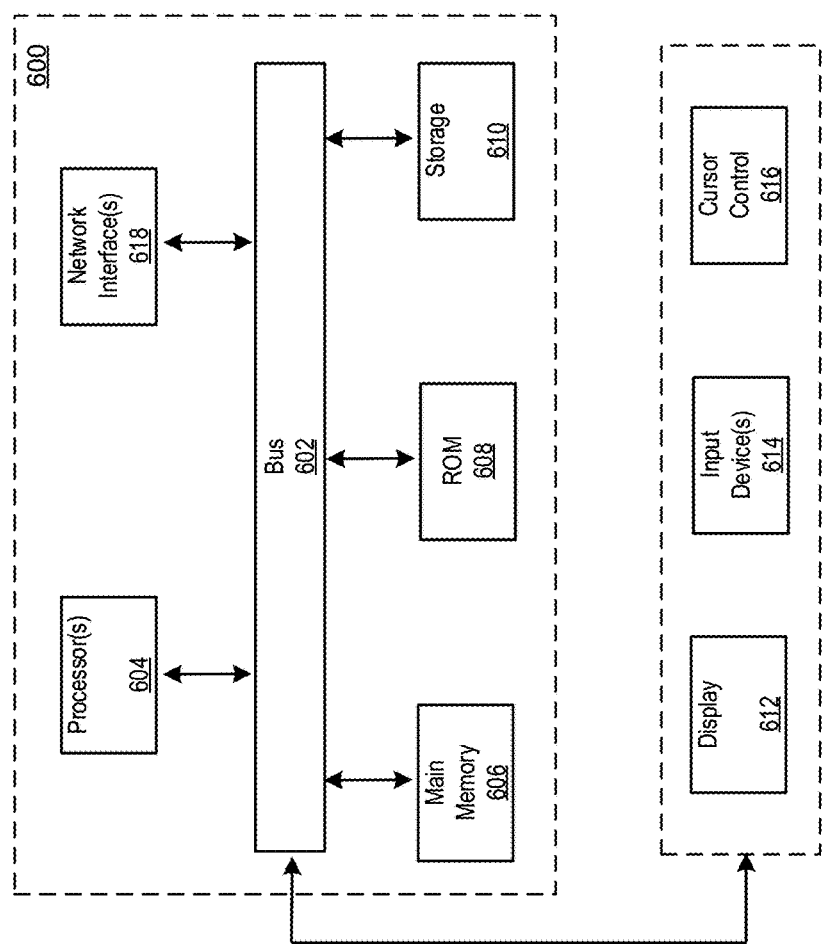
FIG. 6 illustrates an example computing system that may be used in implementing various features of embodiments of the disclosed technology.

For example, supporting documents refers to any medical records/and or billing records that provide documentation for the procedure was performed, including any clinical (medical or surgical) indications for the surgery. This documentation may be used during a final reimbursement determination if SGI may or may not be met.

Where circuits are implemented in whole or in part using software, in one embodiment, these software elements can be implemented to operate with a computing or processing system capable of carrying out the functionality described with respect thereto. One such example computing system is shown in FIG. 6. Various embodiments are described in terms of this example-computing system 600. After reading this description, it will become apparent to a person skilled in the relevant art how to implement the technology using other computing systems or architectures.

FIG. 6 depicts a block diagram of an example computer system 600 in which various of the embodiments described herein may be implemented. The computer system 600 includes a bus 602 or other communication mechanism for communicating information, one or more hardware processors 604 coupled with bus 602 for processing information. Hardware processor(s) 604 may be, for example, one or more general purpose microprocessors and/or specialized graphical processors.

The computer system 600 also includes a main memory 605, such as a random access memory (RAM), cache and/or other dynamic storage devices, coupled to bus 602 for storing information and instructions to be executed by processor 604. Main memory 605 also may be used for storing temporary variables or other intermediate information during execution of instructions to be executed by processor 604. Such instructions, when stored in storage media accessible to processor 604, render computer system 600 into a special-purpose machine that is customized to perform the operations specified in the instructions.

The computer system 600 further includes a read only memory (ROM) 608 or other static storage device coupled to bus 602 for storing static information and instructions for processor 604. A storage device 610, such a SSD, magnetic disk, optical disk, or USB thumb drive (Flash drive), etc., is provided and coupled to bus 602 for storing information and instructions.

The computer system 600 may be coupled via bus 602 to a display 612, such as a transparent heads-up display (HUD) or an optical head-mounted display (OHMD), for displaying information to a computer user. An input device 614, including a microphone, is coupled to bus 602 for communicating information and command selections to processor 604. An output device 616, including a speaker, is coupled to bus 602 for communicating instructions and messages to processor 604.

The computing system 600 may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "component," "system," "database," and the like, as used herein, can refer to logic embodied in hardware or firmware, or to a collection of software instructions, possibly having entry and exit points, written in a programming language, such as, for example, boy Java, Java, C or C++. A software component may be compiled and linked into an executable program, installed in a dynamic link library, or may be written in an interpreted programming language such as, for example, BASIC, Perl, or Python. Components may also be written in a database language such as SQL and/or handled via a database object such as a trigger or a constraint. It will be appreciated that software components may be callable from other components or from themselves, and/or may be invoked in response to detected events or interrupts. Software components configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware components may be comprised of connected logic units, such as gates and flip-flops, and/or may be comprised of programmable units, such as programmable gate arrays or processors.

The computer system 600 may implement the techniques described herein using customized hard-wired logic, one or more ASICs or FPGAs, firmware and/or program logic which in combination with the computer system causes or programs computer system 600 to be a special-purpose machine. According to one embodiment, the techniques herein are performed by computer system 600 in response to processor(s) 604 executing one or more sequences of one or more instructions contained in main memory 605. Such instructions may be read into main memory 605 from another storage medium, such as storage device 610. Execution of the sequences of instructions contained in main memory 605 causes processor(s) 604 to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, such as storage device 610. Volatile media includes dynamic memory, such as main memory 605. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between non-transitory media. For example, transmission media includes coaxial cables, copper wire, and fiber optics, including the wires that comprise bus 602. Transmission media can also take the form of acoustic or light waves, such as those generated during radio-wave and infra-red data communications.

As used herein, the term "or" may be construed in either an inclusive or exclusive sense. Moreover, the description of resources, operations, or structures in the singular shall not be read to exclude the plural. Conditional language, such as, among others, "can," "could," "might," or "may," unless specifically stated otherwise, or otherwise understood within the context as used, is generally intended to convey that certain embodiments include, while other embodiments do not include, certain features, elements and/or steps.

Terms and phrases used in this document, and variations thereof, unless otherwise expressly stated, should be construed as open ended as opposed to limiting. As examples of the foregoing, the term "including" should be read as meaning "including, without limitation" or the like. The term "example" is used to provide exemplary instances of the item in discussion, not an exhaustive or limiting list thereof. The terms "a" or "an" should be read as meaning "at least one," "one or more" or the like. The presence of broadening words and phrases such as "one or more," "at least," "but not limited to" or other like phrases in some instances shall not be read to mean that the narrower case is intended or required in instances where such broadening phrases may be absent.

Although described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the present application, whether or not such embodiments are described and whether or not such features are presented as being a part of a described embodiment. Thus, the breadth and scope of the present application should not be limited by any of the above-described exemplary embodiments.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A method for surgical guideline indicator (SGI) mapping to facilitate automated medical bill adjudication, the method comprising:
   creating a first training set comprising training data of past medical procedure codes and corresponding SGIs determined for the medical procedure codes;
   training a machine learning model in a first stage using the first training set;
   obtaining, by a medical bill analysis device, first and second sets of clinical resource data from first and second data sources, wherein each of the first and second sets of clinical resource data associates SGIs with medical procedure codes;

correlating, by the medical bill analysis device, the SGIs in the obtained clinical resource data to generate and store a mapping of medical procedure codes in the clinical resource data to indications of the appropriateness of an assistant at surgery or a co-surgeon for surgical procedures corresponding to the medical procedure codes by:
   comparing a first SGI from the first set of clinical resource data and a second SGI from the second set of clinical resource data, wherein the first and second SGIs are associated with a same one of the medical procedure codes; and
   storing a mapping of the first SGI with the same one of the medical procedure codes when there is no disagreement between the first SGI from the first set of clinical resource data and the second SGI from the second set of clinical resource data;
analyzing, by the medical bill analysis device, an ingested electronic medical bill associated with an insurance claim by:
   extracting a medical procedure code corresponding to a surgical procedure associated with the ingested electronic medical bill,
   determining whether a mapping is stored for the medical procedure code,
   responsive to determining a mapping is stored for the medical procedure code, selecting the SGI mapped to the medical procedure code according to the stored mapping, and
   responsive to determining no mapping is stored for the medical procedure code, determining an SGI for the surgical procedure associated with the ingested electronic medical bill by applying the trained machine learning model to the extracted medical procedure code;
generating, by the medical bill analysis device, the selected SGI or the determined SGI for the surgical procedure associated with the ingested electronic medical bill;
selecting, by the medical bill analysis device, surgical team services based on the determined SGI for the surgical procedure associated with the ingested electronic medical bill;
generating, by the medical bill analysis device, an automated adjudication recommendation for the medical bill utilizing the selected surgical team services;
outputting, by the medical bill analysis device, the generated automated adjudication recommendation;
receiving user input identifying determined SGIs that are rejected;
creating a second training set comprising determined SGIs that are rejected and corresponding medical procedure codes; and
training the trained machine learning model in a second stage using the second training set.

2. The method of claim 1, wherein the medical procedure codes comprise current procedure terminology (CPT) codes.

3. The method of claim 1, further comprising:
obtaining, by the medical bill analysis device, clinical review data comprising the indication of the appropriateness of the assistant at surgery or the co-surgeon for one of the surgical procedures corresponding to the one of the medical procedure codes, when the determination indicates there is a disagreement between the first SGI and the second SGI.

4. The method of claim 1, wherein the first and second data sources comprise a Centers for Medicare and Medicaid Services (CMS) relative value file and an American College of Surgeons (ACS) Physicians as Assistants at Surgery reference guide.

5. The method of claim 1, wherein the indications of the appropriateness of an assistant at surgery or a co-surgeon for surgical procedures comprise one or more of an indication that industry guidelines for reporting are met, industry guidelines for reporting are not met, or industry guidelines for reporting may be met.

6. A medical bill analysis device, comprising memory comprising programmed instructions stored thereon and one or more processors configured to be capable of executing the stored programmed instructions to:
   create a first training set comprising training data of past medical procedure codes and corresponding SGIs determined for the medical procedure codes;
   train a machine learning model in a first stage using the first training set;
   obtain, by the medical bill analysis device, first and second sets of clinical resource data from first and second data sources, wherein each of the first and second sets of clinical resource data associates surgical guideline indicators (SGIs) with medical procedure codes;
   correlate the SGIs in the obtained clinical resource data to generate and store a mapping of medical procedure codes in the clinical resource data to indications of the appropriateness of an assistant at surgery or a co-surgeon for surgical procedures corresponding to the medical procedure codes by:
     comparing a first SGI from the first set of clinical resource data and a second SGI from the second set of clinical resource data, wherein the first and second SGIs are associated with a same one of the medical procedure codes; and
     storing a mapping of the first SGI with the same one of the medical procedure codes when there is no disagreement between the first SGI from the first set of clinical resource data and the second SGI from the second set of clinical resource data;
   analyze an ingested electronic medical bill associated with an insurance claim by:
     extracting a medical procedure code corresponding to a surgical procedure associated with the ingested electronic medical bill,
     responsive to determining a mapping is stored for the medical procedure code, selecting the SGI mapped to the medical procedure code according to the stored mapping, and
     responsive to determining no mapping is stored for the medical procedure code, determining an SGI for the surgical procedure associated with the ingested electronic medical bill by applying the trained machine learning model to the extracted medical procedure code;
   generate, by the medical bill analysis device, the selected SGI or the determined SGI for the surgical procedure associated with the ingested electronic medical bill;
   select, by the medical bill analysis device, surgical team services based on the determined SGI for the surgical procedure associated with the ingested electronic medical bill;
   generate, by the medical bill analysis device, an automated adjudication recommendation for the medical bill utilizing the selected surgical team services;
   output, by the medical bill analysis device, the generated automated adjudication recommendation;

receive user input identifying determined SGIs that are rejected;

create a second training set comprising determined SGIs that are rejected and corresponding medical procedure codes; and train the trained machine learning model in a second stage using the second training set.

7. The medical bill analysis device of claim 6, wherein the medical procedure codes comprise current procedure terminology (CPT) codes.

8. The medical bill analysis device of claim 6, wherein the processors are further configured to be capable of executing the stored programmed instructions to:

obtain clinical review data comprising the indication of the appropriateness of the assistant at surgery or the co-surgeon for one of the surgical procedures corresponding to the one of the medical procedure codes, when the determination indicates there is a disagreement between the first SGI and the second SGI.

9. The medical bill analysis device of claim 6, wherein the first and second data sources comprise a Centers for Medicare and Medicaid Services (CMS) relative value file and an American College of Surgeons (ACS) Physicians as Assistants at Surgery reference guide.

10. The medical bill analysis device of claim 6, wherein the indications of the appropriateness of an assistant at surgery or a co-surgeon for surgical procedures comprise one or more of an indication that industry guidelines for reporting are met, industry guidelines for reporting are not met, or industry guidelines for reporting may be met.

11. A non-transitory machine readable medium having stored thereon instructions for surgical guideline indicator (SGI) mapping to facilitate automated medical bill adjudication comprising executable code which when executed by one or more processors, causes the processors to:

creating a first training set comprising training data of past medical procedure codes and corresponding SGIs determined for the medical procedure codes;

training a machine learning model in a first stage using the first training set;

obtaining, by a medical bill analysis device, first and second sets of clinical resource data from first and second data sources, wherein each of the first and second sets of clinical resource data associates SGIs with medical procedure codes;

correlate the SGIs in the obtained clinical resource data to generate and store a mapping of medical procedure codes in the clinical resource data to indications of the appropriateness of an assistant at surgery or a co-surgeon for surgical procedures corresponding to the medical procedure codes by:

comparing a first SGI from the first set of clinical resource data and a second SGI from the second set of clinical resource data, wherein the first and second SGIs are associated with a same one of the medical procedure codes; and storing a mapping of the first SGI with the same one of the medical procedure codes when there is no disagreement between the first SGI from the first set of clinical resource data and the second SGI from the second set of clinical resource data;

analyze an ingested electronic medical bill associated with an insurance claim by:

extracting a medical procedure code corresponding to a surgical procedure associated with the ingested electronic medical bill, determining whether a mapping is stored for the medical procedure code, responsive to determining a mapping is stored for the medical procedure code, selecting the SGI mapped to the medical procedure code according to the stored mapping, and responsive to determining no mapping is stored for the medical procedure code, determining an SGI for the surgical procedure associated with the ingested electronic medical bill by applying the trained machine learning model to the extracted medical procedure code;

generate, by the medical bill analysis device, the selected SGI or the determined SGI for the surgical procedure associated with the ingested electronic medical bill;

select surgical team services based on the determined SGI for the surgical procedure associated with the ingested electronic medical bill;

generate an automated adjudication recommendation for the medical bill utilizing the selected surgical team services;

output the generated automated adjudication recommendation;

create a first training set comprising training data of past medical procedure codes and corresponding SGIs determined for the medical procedure codes;

train a machine learning model in a first stage using the first training set.

12. The non-transitory machine readable medium of claim 11, wherein the medical procedure codes comprise current procedure terminology (CPT) codes.

13. The non-transitory machine readable medium of claim 11, wherein the executable code, when executed by the processors, further causes the processors to:

obtain clinical review data comprising the indication of the appropriateness of the assistant at surgery or the co-surgeon for one of the surgical procedures corresponding to the one of the medical procedure codes, when the determination indicates there is a disagreement between the first SGI and the second SGI.

14. The non-transitory machine readable medium of claim 11, wherein the first and second data sources comprise a Centers for Medicare and Medicaid Services (CMS) relative value file and an American College of Surgeons (ACS) Physicians as Assistants at Surgery reference guide.

15. The non-transitory machine readable medium of claim 11, wherein the indications of the appropriateness of an assistant at surgery or a co-surgeon for surgical procedures comprise one or more of an indication that industry guidelines for reporting are met, industry guidelines for reporting are not met, or industry guidelines for reporting may be met.

* * * * *